(12) United States Patent
Oklejas

(10) Patent No.: US 8,151,315 B2
(45) Date of Patent: Apr. 3, 2012

(54) HYBRID AUDIO/VIDEO ENTERTAINMENT SYSTEM

(76) Inventor: Robert A. Oklejas, Monroe, MI (US)

( * ) Notice: Subject to any disclaimer, the term of this patent is extended or adjusted under 35 U.S.C. 154(b) by 316 days.

(21) Appl. No.: 12/564,785

(22) Filed: Sep. 22, 2009

(65) Prior Publication Data

US 2010/0088730 A1 Apr. 8, 2010

Related U.S. Application Data

(63) Continuation-in-part of application No. 11/275,960, filed on Feb. 7, 2006, now abandoned.

(51) Int. Cl.
*H04N 7/16* (2011.01)
(52) U.S. Cl. ......... 725/133; 725/141; 725/146; 725/153
(58) Field of Classification Search .................. 725/133, 725/141, 146, 153
See application file for complete search history.

(56) References Cited

U.S. PATENT DOCUMENTS

| | | | |
|---|---|---|---|
| 5,571,057 A | 11/1996 | Ayers | |
| 6,256,401 B1 | 7/2001 | Whited | |
| 6,414,716 B1 | 7/2002 | Kawai | |
| 6,418,234 B1 | 7/2002 | Whited | |
| 6,489,986 B1 | 12/2002 | Allen | |
| 6,529,233 B1 | 3/2003 | Allen | |
| 6,732,028 B2 | 5/2004 | Vanstory et al. | |
| 7,587,747 B2 * | 9/2009 | Maguire, Jr. | 725/133 |
| 2001/0013680 A1 | 8/2001 | Chaaban | |
| 2002/0028002 A1 | 3/2002 | Whited | |
| 2002/0051958 A1 | 5/2002 | Khalsa | |
| 2002/0171770 A1 | 11/2002 | Wendt et al. | |
| 2004/0032434 A1 | 2/2004 | Pinsky et al. | |
| 2004/0044724 A1 | 3/2004 | Bell et al. | |
| 2004/0044725 A1 | 3/2004 | Bell et al. | |
| 2004/0230486 A1 | 11/2004 | Greenlee | |
| 2005/0078172 A1 | 4/2005 | Harville et al. | |
| 2005/0262542 A1 | 11/2005 | DeWeese et al. | |
| 2006/0176374 A1 * | 8/2006 | Oklejas | 348/211.8 |

FOREIGN PATENT DOCUMENTS

EP 1415470 B1 11/2006

OTHER PUBLICATIONS

Search Report for International Application No. PCT/US2010/048238; mailed Nov. 3, 2010; 2 pages.
Written Opinion for International Application No. PCT/US2010/048238; mailed Nov. 3, 2010; 6 pages.
Article entitled "List of SportsCenter segments and specials" from Wikipedia, the free encyclopedia at http://web.archive.org/web/20071215022309/http://en.wikipedia.org/wiki/List_of_SportsCenter_segments_and_specials#P on Oct. 21, 2010; 7 pages.
Second Written Opinion of the International Preliminary Examining Authority for International Application No. PCT/US2010/048238; mailed Nov. 7, 2011; 22 pages.

* cited by examiner

*Primary Examiner* — Hunter Lonsberry
(74) *Attorney, Agent, or Firm* — Howard & Howard Attorneys PLLC

(57) ABSTRACT

A television entertainment system that combines the visual imagery of television entertainment and transmission with the audio of radio entertainment and transmission to create a new synthesis system for therapeutic benefit designated as Hybrid Radio Television. Each segment (video/audio) of the system can be viewed or heard/listened to on its own, however, it is designed to be viewed and heard/listened to as an integrated whole, as selected by a viewer.

24 Claims, 1 Drawing Sheet

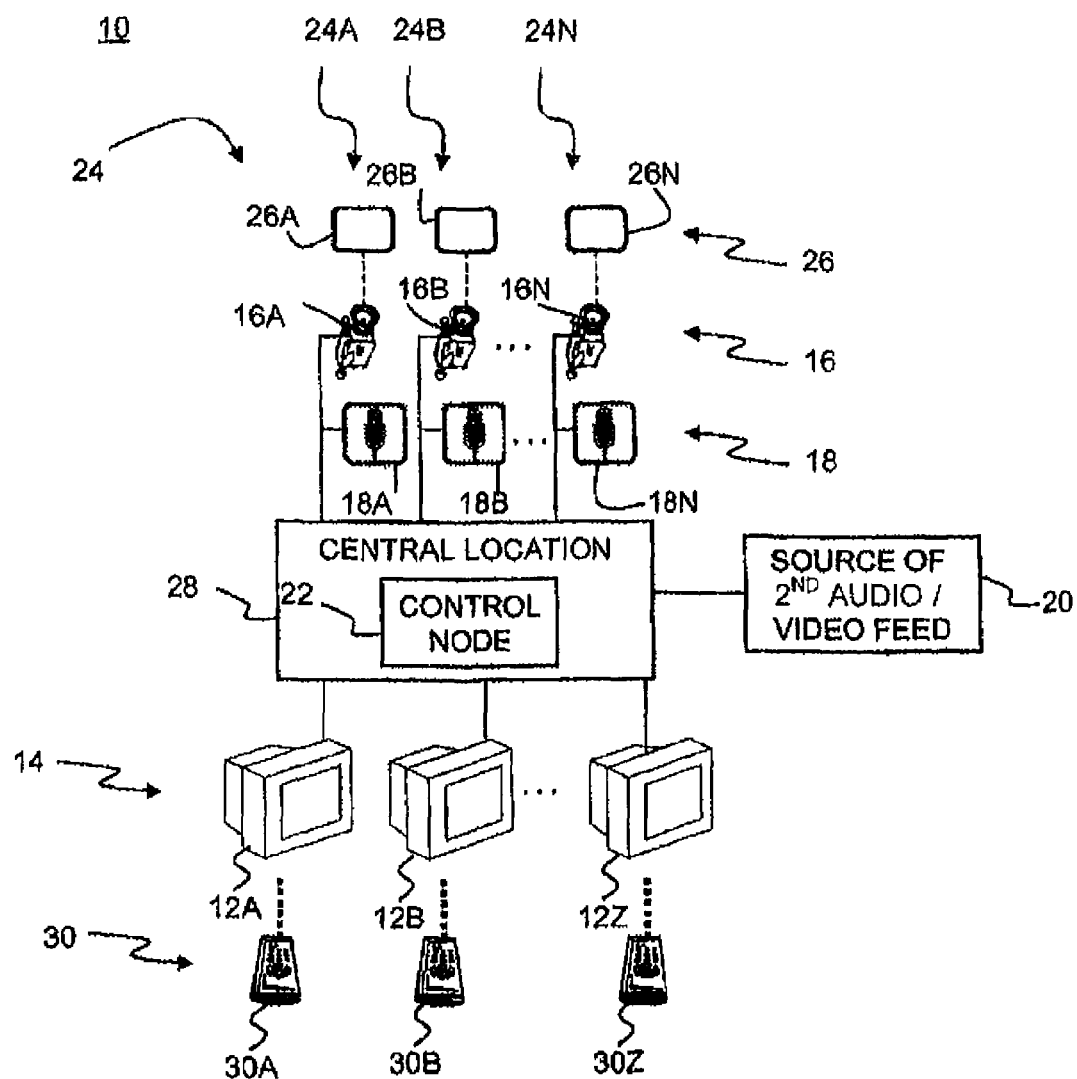

HYBRID AUDIO/VIDEO ENTERTAINMENT SYSTEM

RELATED APPLICATIONS

The present application is a Continuation-In-Part of U.S. application Ser. No. 11/275,960 filed Feb. 7, 2006, which claims priority to U.S. Provisional Patent Application Ser. No. 60/650,674, filed Feb. 7, 2005, the disclosures of which are incorporated by reference.

FIELD OF THE INVENTION

The present invention relates to an audio/video entertainment system, particularly one adapted to delivering therapeutic benefits to the viewer.

BACKGROUND OF THE INVENTION AND ADVANTAGES

In Enerchi Health, a web based health information service, recently it was stated that "People generally feel that they live cluttered, hectic, overwhelming lives; between work, family, and friends, or any of the dozens of things that fill our days and tax our body and mind, rarely do we take even a small part of our waking life entirely for ourselves, apart from unhealthy 'escapist' kinds of relaxation like TV that don't allow the mind to settle down. The almost permanent state of stimulation and stress inevitably has dire consequences for both mental and physical health, from higher blood pressure to compromised immune systems, leaving us vulnerable to any number of conditions. Making a priority of taking 'time out' every day to simply withdraw from the whole mess can be a big step toward improving health."

Frantic programming seeks to draw the viewer to ever narrower fields of interests, but with more intensely focused programming. The result is that there are dozens of entire networks devoted 24 hours per day, seven days per week to a single subject; i.e., The Food Network, Tennis Network, Speed, History Channel, Court TV, etc. Far from producing a mental "time out", current programming adds gasoline to the fire of stress and information overload.

Moreover, there is a large and growing demographic segment that seeks to escape TV entirely, or to only occasionally use it as a quick source of news, in favor of a more tranquil and relaxing lifestyle. This demographic segment includes a mature, upscale audience that appreciates and desires to experience tranquil, relaxing places, preferably with beautiful, breathtaking scenery.

SUMMARY OF THE INVENTION

This new concept or format in television entertainment has as its primary goal the positive therapeutic effects of "time out" that would enhance mental and physical health. This therapeutic television system stands in stark contrast to the current frantic programming that is the norm in TV today and which the aforementioned audience seeks to avoid.

In one aspect of the present invention, a hybrid audio and video system is provided for providing video and/or audio to a display at a remote location in response to control signals received from a user. The system includes at least one camera, a microphone, a source of a second video feed, and a control node. The at least one camera is located at a first location and provides a first video feed of a subject at the first location. The microphone is located at the first location and provides a first audio feed of the first location. The control node is located at a central location and is coupled to the at least one camera, the microphone, and the second video source. The control node receives the control signals and provides a user video/audio feed to the display at the remote location based on the first video feed, the audio feed and/or the second video feed as a function of the control signals.

In another aspect of the present invention, a hybrid audio and video system is provided for providing video and/or audio to a display at a remote location in response to control signals received from a user. The system includes a first feed including a first video signal conveying appropriate visual imagery of a subject for the purpose of creating an aesthetically pleasing and relaxing experience by a user, and a second feed including a second audio signal conveying sound supplemental to the conveyed visual imagery of the first feed. A control device is located at the remote location, and the control signals from the user are received by the control device. A control node is in communication with the control device and located at a central location at which the first and second feeds are received and mixed, the control node having inputs including the first and second feeds and the control signals, and having an output signal including a user feed that includes the mixed first and second feeds, the output signal from the control node being received by the control device. The system also includes a display located at the remote location and coupled to the control device. The visual imagery of the subject and the sound conveyed by the user feed is reproduced by the display, the aesthetically pleasing and relaxing experience of the user a result of the user's exposure to the display during its reproduction of the visual imagery and sound contained in the user feed.

A hybrid audio and video system according to the present invention may optionally include an aspect wherein the second feed includes an audio signal and/or a video signal separately or together conveying commercial advertising content that is included in the user feed and communicated to the user using the display.

BRIEF DESCRIPTION OF THE DRAWINGS

FIG. 1 shows a diagram of one embodiment of the present invention as described below.

DETAILED DESCRIPTION OF THE PREFERRED EMBODIMENTS

With reference to FIG. 1, and in operation, the present invention provides a hybrid audio and video system 10 for providing video and/or audio to a display 12, which includes an associated speaker, at a remote location 14 in response to control signals received from a user. The system 10 includes at least one camera 16, at least one microphone 18, a source of a second video and/or audio feed 20, and a control node 22.

The at least one camera 16 is located at a respective location 24 and provides a first video feed of a subject 26 at the respective location 24. The microphone 18 may also be located at the location 24 for providing a first audio feed of the subject 26 at location 24, but instead may be located at some other location. In the illustrated embodiment, a plurality of cameras 16A, 16B, . . . , 16N (three of which are shown) and a plurality of microphones 18A, 18B, . . . , 18N are located at a plurality of respective locations 24A, 24B, . . . , 24N for providing first video/audio feeds of a respective plurality of subjects 26A, 26B, . . . , 26N.

The control node 22 may be located at a central location 28, such as a central studio. The control node 22 is coupled to the at least one camera 16, the microphone 18, and the second video and/or audio source 20. The control node 22 receives the control signals and provides an output signal including a user video/audio feed to the control device 30 (e.g., the cable or satellite transceiver box) at the remote location 14 based on the first video feed, the first audio feed, and the second video and/or audio feed as a function of the control signals, and the user video/audio feed is conveyed by control device 30 to display 12. The display reproduces the visual imagery and sounds conveyed by the user video/audio feed. The control node 22 receives the various video/audio feeds automatically and/or manually and mixes them, resulting in various output feeds to be delivered to the display(s) 12. The various video/audio feeds may be mixed according to predetermined rules and/or in response to the control signals received from the users.

In one aspect, the user or viewer or consumer controls operation of the system 10 including selecting between channels or feed, or selecting a video-on-demand option on control device 30 and/or creating custom feeds by combining various video and/or audio feeds to create the desired effect (see below). In one embodiment, the user controls the system 10 by sending control signals to the control node 22 via control device 30 at user location 14 to which user/viewer's display 12 is connected. Control device 30A, 30B, . . . , 30Z includes the shown hand-held remote controller as well as the associated digital cable or satellite transceiver unit respectively controlled thereby to which the user/viewer's display 12 is connected. The control devices 30 allow the user to navigate through a series of menus (not shown) presented on the respective display 12A, 12B, . . . , 12Z.

In the illustrated embodiment, at least one of the cameras 16N is a remotely controlled High Definition Television system camera viewing the subject matter 26N. The microphone 18N is working in conjunction with the HDT system camera 16N at locale 24N to acquire the local environmental sounds that are being produced by the subject matter 26N. Such subject matter 26N may be deliberately selected for its aesthetically appealing qualities with an additional emphasis on scenes that produce a relaxation or calming effect on the human psyche. Each such subject matter 26 may include, but is not limited to, a snowy wooded scene, a quiet marina, city skyline, a majestic landscape or seascape, etc. The subject matter 26 may be anywhere in the world and viewed in real time, or at the time of day or night when it was prerecorded.

A common element of these various scenes is that there is no unfolding story to follow, or to miss. The scene preferably provides the viewer with a naturally unfolding scene existing at the locale 24. The scene may present moving elements on which the viewer may focus, such as, for example, a pair of ducks swimming together through a marina, a deer grazing in a meadow, a ship passing through a seascape, a seabird on a beach, etc., but such elements are not distractions in the overall scene, but rather contribute to its tranquility and provide points of interest for the viewer. Moreover, the appearance of such a discrete point of interest is preferably a singular occurrence at any given time in the displayed scene rather than as one of multiple concurrently appearing discrete points of interest, so as not to cause the viewer's attention to be diverted back and forth between two or more such elements, further facilitating the user's relaxation through experiencing the scene. The presence of such elements in the scenes are typically by happenstance, and the camera 16 may be directed to zoom in on the element to satisfy the viewer's natural curiosity about it, or a camera operator/director at location 24 or preferably at central studio 28 may zoom in on the element to bring to the viewer's attention if it otherwise might not be noticed by the viewer. The camera's attention to the point of interest may linger for several minutes before being panned away or zoomed out, or until the element leaves the field of view.

The video and environmental audio output signal (i.e., the first video and/or audio feed) is transmitted from its remote location 24 by either digital satellite or digital cable to the control node 22 or central studio 28 that is also controlling and receiving one or more first feed output signals from other system cameras 16 and microphones 18. At the central studio 28, the incoming video/audio signals (the first video and/or audio feeds) are conditioned (e.g., local environmental sounds may be altered by being muted, eliminated in part or totally, or emphasized) and may be mixed with appropriate audio and/or video feeds from the source of second audio/video feeds 20.

Another embodiment of the hybrid audio/video system 10 would substitute first feeds of prerecorded video and/or audio for the live first feeds of hybrid audio/video system camera 16 and microphone 18 outputs. That is to say, the first audio and/or video feed of such an alternative embodiment utilizes prerecorded video and/or audio instead of live video and/or audio from camera 16 and microphone 18 at a location 24. Essentially the subject matter would remain the same or nearly so and subsequent processing would be the same or nearly the same as well. This version has a start up cost advantage over the multitude of HDT system cameras and microphones version.

The audio and/or video feeds from the second source 20 may include, but are not limited to musical selections and a possible optional human voice spoken by an "on-air" radio personality, and/or an unobtrusive visual superimposition of a banner across the bottom of the scene displaying prestigious brand's mark and/or product depiction. The mark and/or product depiction is preferably still rather than moving, so as not to provide an intrusive distraction from the scene being viewed, with a textually-presented slogan associated with the brand or its associated service or product. The "on-air" radio personality may introduce a programming segment as being sponsored or brought to the viewer by the source of the advertised product or service, and may also, or instead, read the slogan. The user is thus reminded of the brand's service or product. In connection with the present invention, the prestigious brands are used in a style which respects established corporate and product identity, an advantage previously offered only in slick, upscale printed publications.

As noted above, a large and growing demographic segment of TV viewers, in seeking a more tranquil and relaxing lifestyle, are moving away from TV entirely or only occasionally using it as a quick source of news. Individuals in this demographic segment seek freedom from the chaos, fear and stress of everyday life, and to temporarily divorce themselves from certain aspects of their working lives or the world we live in, such as 24 hours news, email, cell phones, text messaging, voicemail, deadlines, travel warnings, etc. This segment tends to be mature and includes a discerning, upscale audience that can appreciate, and recognizes value in, products and services of various types (e.g., luxury-market automobiles or timepieces, premium luggage, business clothing, jewelry, luxury hotel chains and resorts, cruise lines, travel bureaus, etc.) associated with the prestigious, carefully-selected brand advertising that lends itself well to the television format and system of the present invention. Such viewers often seek to experience, and appreciate the benefits of, tranquility and relaxation.

The output signal now consisting of the system or mixed video, and system or mixed audio, is transmitted by digital cable and satellite or Internet to the user/consumer at remote location 14 where it is displayed and may be heard on a display 12. The display 12 may be any appropriate display including but not limited to a television, a computer, or a radio (for audio only).

Thus, an embodiment of the present invention provides a television entertainment system and format that combines appropriate radio/musical entertainment formats with appropriate television visual imagery for the goal of an aesthetically and aurally pleasing and relaxing experience. It should be a therapeutic experience for the viewer. It includes a television entertainment system and format whose purposeful design is to produce effortless calmness and a therapeutic "time out" in the viewer's daily life, and whose viewing does not interfere in other daily activities. The viewing experience is primarily a viewing experience that creates the sense of the viewer being present at the locale, the images and background sounds of which are "live" or prerecorded. The television entertainment production method employs remote controlled cameras to capture the most aesthetically pleasing visuals available at any particular time. It may alternatively be a television program that uses prerecorded videotaped imagery. It may also be a television entertainment method that mixes music, environmental sounds, on-air voice and conversation with aesthetically pleasing visual presentations. It may alternatively be a commercial television entertainment format that allows use of audio/video, audio only and video only commercials or a television/radio format that mixes live locale sounds such as nature, surf, running water, rain, foghorn, or other soothing therapeutic sounds such as music or musical interludes.

The present invention is aimed at providing the positive therapeutic effects of a "time out" that would enhance mental and physical health, by virtually transporting the viewer to another, more relaxing scene, which can be experienced visually and audibly, the effect of which may be enhanced by a supplementing soundtrack of soothing music, for example.

INDUSTRIAL APPLICABILITY

Within recent years a number of technological developments in the electronic and television industry have been introduced on a national basis. These developments are:
1. Large Screen Projection and Plasma Television sets;
2. Digital Satellite and Cable Television; and
3. High Definition Television.

Large Screen television sets make possible movie-like viewing of television programming. The large screen format delivers a life-like or "you are there experience."

Both satellite and cable digital television transmission systems now allow the capacity to simultaneously transmit up to 1500 channels. The sheer number of channels has resulted in a frantic search for content to fill this huge capability. Yet, content demand has not been satisfied as hundreds of channels are unused, thus making it possible to deliver nontraditional niche programming. Digital transmission has also dramatically improved picture and sound quality, again adding to the possibility of a "you are there experience."

High Definition Television systems deliver a picture quality that is indistinguishable from real viewing to add significantly to a "you are there experience."

The present invention creates a hybrid audio/video or Hybrid Radio Television ("HRT") system 10 and an experience for the viewer, at selected intervals chosen by the viewer, for realizing a therapeutic and relaxation benefit, selected on the basis of the preferences of the individual viewer or a group of viewers.

HRT Technical Considerations—Two main technical tasks required by the hybrid audio/video system are content acquisition and delivery. An important aspect of the most appealing format is the "live" presentation. It has long been recognized that "live" television creates the most interest and emotional connection to the viewer that tape or film simply cannot deliver. For instance it has been noted that television coverage of the 9-11 terrorist attacks noted that viewers in real time (live) experienced the same physical effects (elevated heart rate, sweating, and agitation) and psychological effects (fear, anxiety) as the witnesses in New York City. The similar but opposite effect of live scenes of aesthetically pleasing and relaxing content produces therapeutic calming effects as if the viewer was at each of these pleasant locales. Cameras in a number of different locales can be controlled remotely from a central studio. Similar to coverage of a golf tournament in which the coverage constantly changes from hole to hole to keep up a rhythm of action, the hybrid audio/video system director will constantly seek out the most interesting, dramatic, and appealing shots from locale to locale, etc. The live coverage can be supplemented by prerecorded footage as needed, for instance as a particularly dramatic introduction to a new locale.

Sight and Sound—The camera work of the hybrid audio/video system will often focus on single scene for prolonged periods of time (as compared to conventional television). For instance, a sunset scene may be viewed without any camera motion for 30 minutes or more. For a lighthouse subject format, the television camera may not change the scene for hours at a time. In other scenes that offer a less focused subject than a sunset or lighthouse, for instance a major cityscape, the camera will often stay motionless on a scene for a few minutes, but then slowly pan in different directions. Scene shifts between different locales will be accomplished with deliberate slowness, with time intervals between different locales measured in minutes to tens of minutes.

For scenes involving ship watching, the camera can acquire the ship at a great distance (e.g., as it emerges over the horizon) with telephoto lenses and then follow the vessel as its image grows in size, until close-ups of various parts of the ship are possible. This camera view can last for an hour or more. Information about the ship, such as type, registry, tonnage, propulsion, etc., can be displayed at the edges of the screen. Similar data can also accompany land scenes, such as what city, island, mountain, and locale is being viewed.

Although a hybrid audio/video system entertainment places a large focus on radio (audio) format of music and "on-air personality" conversation, another dimension of sound can be added to the format by including appropriate sounds from the locale either between musical accompaniments or mixed with the music. These sounds can convey the additional impression of "you are there," or enhance it. These sounds can be selected for their relaxation/therapeutic effects, sounds such as surf, running water, rain, bird songs, etc. Other sounds such as lighthouse fog horns, ship whistles, weather sounds of wind, thunder can add to the realism and authenticity of the video presentation.

"On-air personalities" will provide continuity and additional interest to the visual/audio signals by providing entertaining conversation, information, and the calming soothing effective of the human voice. Information about the visual or music selection or artist can also be offered. In addition, traditional radio services such as weather, traffic, and even news may be provided where hybrid audio/video system entertainment is provided on a local or regional basis.

The method that will achieve the goal of therapeutic television is to combine visual imagery conveyed by primarily live television broadcast that are esthetically pleasing (beautiful architecture, cityscapes, harborscapes, landscapes and seascapes), yet purposefully calming to the human psyche (no drama, comedy, adventure, or any other forms that are designed to engage the viewer), with voice and music (with similarity to music therapy) that are also designed for calmness and relaxation. The audio portion of the programming is much like radio in that it can stand on its own as an entertainment format Likewise the visual imagery stands on its own, yet is connected to the audio to create a sense of beauty and tranquility. This relationship between a radio-like format and the visuals of television is part of the Hybrid Radio Television system or HRT system.

To give a sense of the HRT system programming, it can be described as follows—you are viewing through a window a beautiful, interesting land/sea/city/harbor scene while listening to your favorite music or radio program. It is as if you lived in the most desired locations in the world—a South Pacific isle, Nob Hill in San Francisco, downtown Chicago, or the Canadian Rockies, when in fact you are watching these scenes in your own home, preferably but not necessarily on a large screen HDTV television. These scenes and the voice and/or music accompaniment are not imperative to watch or listen to. The users can watch/listen as they choose. The HRT system does not, unlike conventional television programming, demand your attention and is non-intrusive. The user will not have the frustration of missing some moment of dialogue or plot or action sequence because, although the scenes change (slowly), the effect of purposeful calmness and aesthetic fulfillment remains constant. HRT system therapeutic television can be on during conversation, dinner, or while you read or work. There is no story-line to follow. And that is by design, while the design intent of "demanding television" is to make it difficult to impossible to engage in any of the above. Even programs on relaxation therapy such as yoga or exercise programs still require you to focus and think about what is being presented. Some of those programs may be related to relaxation, while the HRT system actually is therapy and relaxation.

As the user enjoys the visual programming content, all the while appropriate music such as, for example, cool jazz, easy listening, classics, soft rock, contemporary pop, orchestrated classical, new age, or performances by vocalists or instrumental soloists, is offered up by a deep melodious voiced "on-air" personality, or solely choreographed without any human voices interposed. Preferably, all audio content received by the user is all designed to be aurally pleasing and relaxing.

A number of the following specific system formats suggest themselves as appropriate for HRT system therapeutic television, but it is to be understood that the inventive system is certainly not limited thereto. Each format may be provided to the viewer via one of a plurality of dedicated channels, each dedicated channel delivering programming of a particular scene or type of scene 24/7, or may be provided to the viewer on-demand through menu selections via control device 30.

HRT Cityscapes and Harborscapes—This HRT system program format features the world's most spectacular city and harbor scenes—New York, San Francisco, Hong Kong, etc—spectacular skylines, building architecture, ships from the far corners of the world arriving and departing. Sunsets and sunrises on the Golden Gate, the Bosporus, Rio de Janeiro, are the visuals of the HRT system in this format. In Chicago, New York, or any other great city for that matter, the most sought-after residences are luxury apartment/condominiums with a great view. Ten thousand dollars a month for rent is typical for these addresses. This is what cityscapes and harborscapes can deliver to a viewer anywhere in the world. One can enjoy hours, an hour, a few minutes, or any selected amount of time of detachment, relaxation and enjoyment watching sunset and nightfall in San Francisco, or watching ships or planes departing and arriving from world destinations. All of the scenes and music are beautiful and endlessly interesting, but none are imperative to watch. The HRT system will always be there, 24 hours per day, seven days per week, whenever the viewer wants it, which may be in real time or time shifted.

HRT Ship Channel—This HRT system format is closely related to cityscapes, but with an emphasis on ship watching. So in addition to the great port cities of the world, additional live cameras can cover ships transiting and locking through canals and waterways (Suez Canal, Well and, St. Lawrence, Sault St. Marie, Kiel, etc.). In the Great Lakes area, ship watching is a very popular pastime. Hundreds of thousands of people travel hundreds of miles to the lock system at Sault Step. Marie, Mich., or viewing locations at hotels and motels along the St. Claire River for this activity. Watching ships passing the backdrop of the Detroit skyline, from viewing locations across the Detroit River in Windsor, Ontario, Canada, can also be a relaxing and interesting pastime. The HRT system can bring an electronically enhanced ship watching experience to people thousands of miles from the nearest ocean or port, including the possibility of watching these scenes in real time or time shifted, as desired.

HRT Ships at Sea—Imagine the sense of relaxation the view from a river boat cruise can offer. With the ships at sea HRT system format, the viewer can float down the Mississippi, the Nile, the (Blue) Danube, the Rhine, the Volga, or any other of the world's great rivers flowing past the captivating countryside and cities of those far away and exotic locales. By placing television cameras on ships and cruise boats, the HRT system's ships at sea format can get you there as you watch the wake of your ship meet the horizon, accompanied by your favorite music.

HRT Tropical Paradise—In this HRT system format the viewer sees palm trees bending and swaying into the wind overlooking a full moonlit beach, while the sounds of the surf creates a soothing background for the musical accompaniment. This format should be one of the most powerful HRT system formats in achieving a therapeutic "time out."

HRT Lighthouses—Lighthouse tourism and collectables is a major cottage industry in the US. Many have a mystical attraction to these sentinels of the sea and what better way to fulfill that yearning than to live by one courtesy of a large high definition HRT experience. HRT Lighthouses will be one of the formats where the camera scene can remain substantially motionless for hours on end.

Simulcasting Regional and Local HRT—Because the HRT system is politically and culturally neutral, the potential scale of delivery is worldwide. The HRT system format though, also allows for local content, as the HRT system can easily incorporate local commercials as well as local content. For instance, a Great Lakes version of the HRT system can be simulcast with a radio format such as the locally produced portion of a popular Detroit radio station. Thus, the second audio feed may include a simulcast with a locally or regionally-produced radio broadcast. The radio broadcast may be local or regional relative to the location of the user, or alternatively, it may be local or regional relative to the location of the scene being viewed, contributing to the "local flavor" provided by the programmed imagery. For example, evening skyline scenes of San Francisco may be accompanied by a simulcast of a San Francisco jazz radio program, perhaps including commentary by its local on-air host contributing to the user's "you are there experience" despite the user being geographically remote from San Francisco. Local radio personalities can use the visuals of the HRT system as a compliment to their topics of discussion. The simulcast can be delivered via local cable distributors.

Regional and Local HRT may also include tranquil scenes of the local city which the viewer normally does not get the opportunity to experience. While the city in which the viewer is located may, in his everyday life, be a hectic and stressful place from which he would like to escape, it is expected that presenting tranquil scenes of it at certain locations (e.g., a downtown riverfront or a park) and/or time of day (e.g., early morning or sunset) at which it is quiet and devoid of hustle and bustle, and quite different from the viewer's normal, real-life exposure to the same environs, would improve his perceptions of it. Experiencing the locality in which the viewer lives and works and ordinarily perceives as a source of stresses in his life, as a tranquil, relaxing, and beautiful place, would tend to improve the user's outlook about living and working there.

Revenue and Commercials—The HRT system may be designed to be a basis for a profit-making business. As such, ad revenue generating commercials may be integrated as a part of the programming. To maintain and even enhance the HRT system therapeutic television experience, commercials will follow guidelines of style and content that will reinforce the HRT system programming experience. Including, but not limited to:

1. Traditional audio and video content commercials, preferably complementary in style and tone to the programming content. Such commercials may be interposed between programming segments or pluralities of sequential segments, each segment lasting, for example, the duration of one or more musical selections, or the amount of time associated with completion of a viewed event such as the passing of a ship through a scene or the duration of a sunset;

2. Audio only—for instance the "on-air personality" can read a commercial while the visuals of the current HRT system locale are still playing. This is an original development in TV commercials in which sound only conveys the commercial content while the "entertainment" video portion remains basically unchanged;

3. Visual only—a sponsor's company or corporate logo (for a time period of 15-30-60 minutes) may be displayed unintrusively in the corner of the screen;

4. Seamless embedded commercial—the commercial can be integrated into the programming virtually seamlessly—for instance an HRT system segment may be using downtown Chicago as its viewing locale or a cruise ship departing port. The Chicago city convention and tourism bureau and the cruise line are beneficiaries of the television exposure and may pay for additional or increased exposure; or 5. Segment sponsorship introduction—as described above, a banner can be unobtrusively superimposed across the bottom of the scene displaying a brand's mark and/or product depiction, with a textually-presented slogan that may be read by the "on-air" radio personality in introducing the sponsored programming segment.

Due to the lengthy duration of scenes included in the programming according to this format, it may be preferable that commercial content, particularly traditional audio and video commercial content that is interposed and therefore interrupts the programming content, be front-loaded for exposure to the user upon his selecting a particular channel or video-on-demand for viewing, thereby ensuring that the user is both reminded of the goods or services offered by the sponsor, and can thereafter enjoy a relatively longer, uninterrupted period of enjoying the scene and accompanying music.

In a first aspect of the present invention, the system 10 may provide a radio/television format that combines appropriate audio music and voice inputs with appropriate visual imagery for the purpose of creating an esthetically pleasing and relaxing experience.

In a second aspect of the present invention, the system 10 may provide a radio/television entertainment format whose purposeful design is to produce an effortless calmness and a therapeutic mental rest in the viewer's daily life.

In a third aspect of the present invention, the system 10 may provide a radio/television entertainment format that is non intrusive to the viewers attention and allows the viewer to conduct other activities such as reading or conversation.

In a fourth aspect of the present invention, the system 10 may provide a radio/television broadcast that is primarily live for maximum emotional connection, interest and therapeutic effect.

In a fifth aspect of the present invention, the system 10 may provide a radio/television entertainment production in which the scene can remain unchanged for minutes to hours at a time.

In a sixth aspect of the present invention, the system 10 may provide a radio/television entertainment format that allows the use of audio/visual, audio only, and visual only commercials.

In a seventh aspect of the present invention, the system 10 may provide a radio/television format that mixes live locale environmental sounds such as sounds of surf, running water, rain, thunder, fog horns, ships or locomotive engines into the program of music and interludes.

It will, of course, be understood that the foregoing description is of a preferred exemplary embodiment of the invention and that the invention is not limited to the specific embodiments shown. Other changes and modifications will become apparent to those skilled in the art and all such changes and modifications are intended to be within the scope of the present invention.

The invention claimed is:

1. A hybrid audio and video system for providing video and/or audio to a display at a remote location in response to control signals received from a user at the remote location, comprising:
   a first feed including a first video signal conveying appropriate visual imagery of a subject for the purpose of creating an aesthetically pleasing and relaxing experience by a user;
   a second feed including a second audio signal conveying sound supplemental to the conveyed visual imagery of the first feed;
   a control device located at the remote location, the control signals from the user received by the control device,
   a control node in communication with the control device and located at a central location at which the first and second feeds are received and mixed, the control node having inputs comprising the first and second feeds and the control signals, and having an output signal comprising a user feed that includes the mixed first and second feeds, the output signal from the control node received by the control device; and
   a display located at the remote location and coupled to the control device, the visual imagery of the subject and the sound conveyed by the user feed reproduced by the display, the aesthetically pleasing and relaxing experience of the user a result of the user's exposure to the display during its reproduction of the visual imagery and sound contained in the user feed.

2. The hybrid audio and video system of claim 1, wherein the first feed further includes a first audio signal conveying local environmental sounds of the subject, the first audio signal included for the purpose of creating an aurally pleasing and relaxing experience by a user.

3. The hybrid audio and video system of claim 2, wherein the user feed comprises an altered first audio feed in which the local environmental sounds have been conditioned, the conditioned local environmental sounds having been one of muted, eliminated in part or totally, and emphasized.

4. The hybrid audio and video system of claim 1, wherein the visual imagery of the subject and the sound conveyed by the user feed is reproduced using the display to produce an effortless calmness and a therapeutic mental rest in the user's daily life.

5. The hybrid audio and video system of claim 1, wherein the visual imagery of the subject conveyed by the user feed and reproduced using the display can remain substantially unchanged for minutes to hours at a time.

6. The hybrid audio and video system of claim 1, wherein the second audio feed includes an audio signal conveying sound for a purpose including creating an aurally-pleasing and relaxing experience by the user.

7. The hybrid audio and video system of claim 6, wherein the second audio feed further includes an audio signal conveying human voice sounds for a purpose of communicating information to the user about at least one of the visual imagery or music selection conveyed by the user feed and reproduced using the display, the artist of a music selection conveyed by the user feed and reproduced using the display, and traditional radio service information conveyed by the user feed.

8. The hybrid audio and video system of claim 1, wherein the second feed includes a second video feed including a video signal conveying information to the user about at least one of the subject and sponsorship of the visual imagery and/or sounds included in the user feed and reproduced using the display.

9. The hybrid audio and video system of claim 1, wherein the second feed includes a second audio feed and/or a second video feed separately or together conveying commercial advertising content that is included in the user feed and communicated to the user using the display.

10. The hybrid audio and video system of claim 9, wherein the user feed includes traditional commercial advertising content including audio and video signals interposed between programming segments containing aesthetically and aurally pleasing imagery and sounds.

11. The hybrid audio and video system of claim 9, wherein the second feed includes a second video feed comprising a video signal that is superpositioned over a portion of the visual imagery included in the user feed and reproduced using the display.

12. The hybrid audio and video system of claim 11, wherein the superpositioned video signal contains programming sponsorship information communicated to the user using the display.

13. The hybrid audio and video system of claim 9, wherein the second feed includes a second audio feed including the voice of an "on air" personality communicating programming sponsorship information to the user using the display.

14. The hybrid audio and video system of claim 9, wherein the commercial advertising content included in the user feed and communicated to the user using the display identifies prestigious brands and is used in a style which respects established corporate and product identity associated with the brand.

15. The hybrid audio and video system of claim 1, wherein the user feed contains live first video feed.

16. The hybrid audio and video system of claim 1, wherein the user feed contains live first audio feed.

17. The hybrid audio and video system of claim 1, wherein the user feed contains prerecorded first video feed.

18. The hybrid audio and video system of claim 1, wherein the user feed contains prerecorded first audio feed.

19. The hybrid audio and video system of claim 1, wherein the second feed includes prerecorded video and/or audio signals.

20. The hybrid audio and video system of claim 1, wherein the second feed includes a second audio feed that is a simulcast of a radio broadcast, the radio broadcast included in the user feed and reproduced using the display.

21. The hybrid audio and video system of claim 20, wherein the simulcast included in the second audio feed is of a radio broadcast produced locally or regionally relative to the subject of the visual imagery included in the user feed and reproduced using the display.

22. The hybrid audio and video system of claim 20, wherein the simulcast included in the second audio feed is of a radio broadcast produced locally or regionally relative to the remote location of the user.

23. The hybrid audio and video system of claim 1, wherein the visual imagery of the subject and the sound conveyed by the user feed and reproduced using the display is nonintrusive to the user's attention and allows the user to conduct other activities such as reading or conversation.

24. The hybrid audio and video system of claim 1, wherein the visual imagery of the subject conveyed by the user feed is primarily live for maximum emotional connection, interest and therapeutic effect when reproduced using the display.

* * * * *